(12) United States Patent
Solomon et al.

(10) Patent No.: US 11,521,515 B2
(45) Date of Patent: Dec. 6, 2022

(54) STEREOPHONIC APPARATUS FOR BLIND AND VISUALLY-IMPAIRED PEOPLE

(71) Applicant: Can-U-C Ltd., Holon (IL)

(72) Inventors: Leeroy Solomon, Holon (IL); Doron Solomon, Holon (IL)

(73) Assignee: Can-U-C Ltd., Holon (IL)

( * ) Notice: Subject to any disclaimer, the term of this patent is extended or adjusted under 35 U.S.C. 154(b) by 0 days.

(21) Appl. No.: 16/787,256

(22) Filed: Feb. 11, 2020

(65) Prior Publication Data

US 2020/0258422 A1   Aug. 13, 2020

Related U.S. Application Data

(60) Provisional application No. 62/804,568, filed on Feb. 12, 2019.

(51) Int. Cl.
| | |
|---|---|
| G09B 21/00 | (2006.01) |
| H04S 7/00 | (2006.01) |
| H04S 1/00 | (2006.01) |
| G10L 21/0232 | (2013.01) |
| G10L 13/00 | (2006.01) |
| G06V 10/40 | (2022.01) |
| G06V 40/16 | (2022.01) |
| G10L 21/0208 | (2013.01) |
| G06V 30/10 | (2022.01) |

(52) U.S. Cl.
CPC .......... *G09B 21/006* (2013.01); *G06V 10/40* (2022.01); *G06V 40/172* (2022.01); *G10L 13/00* (2013.01); *G10L 21/0232* (2013.01); *H04S 1/007* (2013.01); *H04S 7/303* (2013.01); *G06V 30/10* (2022.01); *G10L 2021/02082* (2013.01); *H04S 2400/11* (2013.01); *H04S 2400/13* (2013.01); *H04S 2400/15* (2013.01)

(58) Field of Classification Search
CPC ... G09B 21/006; G10L 13/00; G10L 21/0232; G10L 2021/02082; G10L 21/0208; G06K 9/00288; G06K 9/46; G06K 2209/01; G06K 9/00355; G06K 9/00684; H04S 7/303; H04S 1/007; H04S 2400/15; H04S 2400/11; H04S 2400/13; H04S 7/302; H04R 2205/041; H04R 1/1041; H04R 5/033; H04R 2460/07
USPC ....................................................... 340/4.14
See application file for complete search history.

(56) References Cited

U.S. PATENT DOCUMENTS

| | | | |
|---|---|---|---|
| 2014/0085446 A1* | 3/2014 | Hicks ................... | G09B 21/008 348/62 |
| 2017/0228597 A1* | 8/2017 | Wexler ............... | G06K 9/00335 |
| 2018/0014130 A1* | 1/2018 | Lunner .................. | A61F 11/06 |
| 2018/0310116 A1* | 10/2018 | Arteaga ................ | G06T 19/006 |
| 2019/0290492 A1* | 9/2019 | Hendrix .................. | G06F 3/165 |
| 2020/0104194 A1* | 4/2020 | Chalmers .............. | H04L 51/224 |

* cited by examiner

*Primary Examiner* — Hirdepal Singh
(74) *Attorney, Agent, or Firm* — Eva Taksel

(57) ABSTRACT

A method and a wearable system which includes distance sensors, cameras and headsets, which all gather data about a blind or visually impaired person's surroundings and are all connected to a portable personal communication device, the device being configured to use scenario-based algorithms and an A.I to process the data and transmit sound instructions to the blind or visually impaired person to enable him/her to independently navigate and deal with his/her environment by provision of identification of objects and reading of local texts.

23 Claims, 5 Drawing Sheets

STEREOPHONIC APPARATUS FOR BLIND AND VISUALLY-IMPAIRED PEOPLE

FIELD OF THE INVENTION

The present invention relates generally to the field of digital medicine and more specifically to methods and apparatus for assisting visually-impaired people.

BACKGROUND OF THE INVENTION

Since the dawn of science, humanity has been trying to face and to find solutions for blindness and visual impairment. It was always difficult for blind and visually impaired people to coexist with the many dangers that their environment offers, but today the environment is more dangerous than ever, because of the many roads, the fast traffic and more. The blind and visually impaired people today have real difficulty with integration in society.

Worldwide Statistics indicates the existence of over 340 million visually impaired people and over 39 million blind people.

According to a new article published in the medical journal: "Lancet Global Health" the researchers from the university "Anglia Ruskin" in England, claimed that the number of blind people in the world would rise to 115 million by 2050. The researchers have gathered data from 188 countries. Professor Rupert Bourne, the chief of the research, claims that there is a high possibility that the number of blind people may even grow to 550 million by 2050. "Even light visually impairment could have a major impact on the person's life. It may be expressed in a reduction of their independent actions, such as prohibition to drive." said Bourne.

The solutions today for the blind and visually impaired are a walking stick, a guide dog, applications on the Smartphone and recently pricey devices which read texts and improving the visually impaired person's vision.

All the systems currently at the market are mostly only for the visually impaired and the price range is between 3,055 Euros (3500 dollars) to 130,944 Euros (150,000 dollars) which most of the people can't afford.

By the mentioned above, There is a need for a system which will give the blind and visually impaired persons the ability to walk independently, read texts and identify objects in a reasonable price, because there aren't any solution that do so. There is a high amount of people who need this kind of solution in a price they could purchase, and this trend is growing.

Bats are visionless creatures and they are one of the few mammals that may use sound to navigate-echolocation, and they rely on that to detect obstacles, find their way and forage for food. Echolocation is the use of sound waves and echoes to determine where objects are in space. Bats use echolocation to navigate and find food in the dark. To echolocate, bats send out sound waves from the mouth or nose. When the sound waves hit an object they produce echoes. The echo bounces off the object and returns to the bats' ears. Bats listen to the echoes to figure out where the object is, how big it is, and its shape.

Using echolocation, bats may detect objects as thin as a human hair in complete darkness. Echolocation allows bats to find insects the size of mosquitoes, which many bats like to eat. Bats are able to adapt to every environmental situation, scenario and event and use their echolocation abilities differently according the specific scenario.

Echolocation calls are usually ultrasonic ranging in frequencies from 20 to 200 kilohertz. In terms of pitch, bats produce echolocation calls with both constant frequencies (CF calls) and varying frequencies that are frequently modulated (FM calls). Most bats produce a complicated sequence of calls, combining CF and FM components. Although low frequency sound travels further than high-frequency sound, calls at higher frequencies give the bats more detailed information—such as size, range, position, speed and direction of a prey's flight. In terms of loudness, bats emit calls as low as 50 dB and as high as 120 dB. The bats use echolocation schemes according to actual scenarios in real-time, which change according to the situation of the environments and the bats' wishes or aims.

The ears and brain cells in bats are especially tuned to the frequencies of the sounds they emit and the echoes that result. A concentration of receptor cells in their inner ear makes bats extremely sensitive to frequency changes.

Humans' hearing is stereophonic and it may detect tunes in different frequencies and volumes (ranging from 10-150 dB). The humans' hearing may detect frequencies between the ranges of 20 Hz to 20 KHz in grownups and in children up to 40 KHz.

Because of his hearing capabilities, the human may detect the direction and the range from a sound source, and it is possible to identify the differences between different sounds/voices. From that, humans may have understanding capabilities about their environment by sounding. Since a human comprises two ears, the human may be provided with 20,000 x2 x10 bits/second=400,000 bits/second of sound data. This is equal to a low video resolution, which is sufficient to function. Therefore, humans could function as if they could see, based on their hearing like the bat.

There thus remains an unmet need to provide systems and methods to assist visually-impaired people.

SUMMARY OF THE INVENTION

It is an object of some aspects of the present invention to provide systems, methods, devices and software for improving the quality of life for blind and visually impaired people.

The current invention provides a system and a method for processing information and data collected from sensors, transmitting the data as semi-raw data by audio to a user, in which his/her mind/brain is able to process, thereby providing him/her with an understanding of the surrounding environment by "seeing via hearing". In some embodiments of the present invention, improved methods and apparatus are provided for improving quality of life for sight-impaired people or users, to give them the same opportunities as an ordinary person.

The present invention provides a method and a wearable system which includes distance sensors, cameras and headsets, which all gather data about a blind or visually impaired person's surroundings and are all connected to a portable personal communication device, the device being configured to use algorithms and an A.I to process the data and transmit sound instructions to the blind or visually impaired person to enable him/her to independently navigate and deal with his/her environment by provision of identification of objects and reading of local texts.

According to some embodiments of the present invention, the system uses echolocation, which herein is using sounds to determine where objects are located in three dimension space.

According to some embodiments of the present invention, the system uses any dedicated computing platform or a Commercial off-the-shelf (COTS) computing platform such as cell phones, single-board computer (SBC) like Raspberry Pi platforms, PC104 computers and other computing platforms such as netbooks/laptops computers and so on.

According to some embodiments of the present invention, the system uses algorithms or apps based on Scenarios that operate on data that are collected from sensors. The Scenarios may be depicted by user intervention or commands or by policy or by context derived by AI decision based on the data that are collected from sensors.

According to some embodiments of the present invention, a scenario is a proper situation and purpose that a blind or visually impaired user is stand in front of. For example, if a blind or visually impaired user's intent is to walk in a street to navigate safely to a specific end point destination, then a GPS navigation SW with voice direction commands with data from GPS module may be operate with distance sensors like Lidar or ultrasonic distance sensors combining data from cameras to identify sidewalk routes with AI SW to insure that a blind or visually impaired person walks according the routes of the sidewalk.

When reaching to cross a road, the AI detects a road ahead and notifies the blind or visually impaired person. The scenario is changed to a road crossing scenario when the AI detects cars, traffic lights on which give verbally the color of the traffic lights and notifying when start and stop the car roads and if the cars respond and stops. All this is accompanied with compass and acceleration meters in order to validate course and even read street signs. Another scenario is the situation when a blind or visually-impaired user gets inside a building then the navigation by GPS ends and relay on AI that detects lamp lights and other not moving reference points that are fuse with data from compass, altimeter and acceleration sensors to measure the location. With AI, identification of doors and elevators and walls is made to guide a blind or visually impaired user to his/her destination in the building.

When getting into an elevator, the system needs to identify it and go to an elevator scenario, the AI camera needs to identify the elevator doors if open or close and where is the elevator command panel, the numbers of the buttons that the user is aiming and read it, identified the floor number and notify verbally and so on. Another example of situation is when a blind or visually impaired user is walking near a pool, the surface of water seems to a distance sensor like Lidar and ultrasonic as a floor, but the AI camera may detect the edge of the pool and may notify upon the danger.

Another example of scenario is when a blind or visually impaired person cooks a stew. A blind or visually impaired person put some groceries on a table and the system gives instructions to a blind or visually impaired person upon each component its identification and location on a table.

According to some embodiments of the present invention, the system uses echo and noise cancelation so that the system removes sounds that are identified as noises and the user may get the surround sound information clearly.

By giving the blind people the ability to function like ordinary people, society and the state will benefit from this change. The blind and visually impaired will not be a burden because society will not have to spend on welfare and nursing for them and also the blind and visually impaired could easily enter the normal work cycle and thus increasing productivity. The groundbreaking system is wearable and collects data about the environment through its sensors and transmits the information to the person in a unique way be could identify, read and walk as though he could see. The product is designed for mass-manufacturing. The revolutionary system is low cost comparing to competitors and affordable.

Echolocation is the use of sound to determine where objects are in space. Because of his hearing capabilities, the human may detect the direction and the range from the sound source, and it is possible to identify the differences between different sounds/voices. The system contains several different types of distance sensors (ultrasonic, LIDAR etc.), camera, neural network for identifying objects and reading texts and Can-U-C's algorithms. The system gathers data from the sensors in medium Bandwidth of dozens MBPS as video, length and location. The system processes the data and transmits it in analog audio in a rate up to 400 KBPS which is equivalent to low resolution video but enough to understand the environment. It is possible to settle even in smaller bandwidths as 50 KBPS for functioning. The system encodes the information: location, speed, direction and more and transmits it to the person in a way his mind could process it quickly and intuitively based on scenarios that the blind or visually impaired person is situated.

In other embodiments of the present invention, a method and system is described for providing process that manage and orchestrate a scenario-based operation of a system. This managing may be algorithm for handling the tasks of the OS and Device management Component so that it may handle the data that are collected from sensors and devices so that the processes hearing data is delivered according Scenarios that the blind or visually impaired person is situated.

In additional embodiments of the present invention, the method includes at least a two-part scenario management component (algorithms). The first part is a scenario identification component that is software whose purpose is to decide which scenario identity to be operated at a specific situation, either by policy or context based on data that are collected from sensors, or by user intervention or commands.

This software may be a part of the OS of the system or as a part of the main application of the system. Based on that Scenario, the second part is the implementation component of appropriate applications to scenario; applications configuration that makes a configuration of algorithms or sub scenario applications to run as a full configuration. The configuration of apps and algorithms serves according the scenario, when the sensors collect data that are fused together by the OS and applications that are running as an implementation of scenario configuration.

In further embodiments of the present invention, the system may operate or includes optional outside system remote sensors and peripheral devices that may be used as part of the system or even used as integral parts of it.

The following embodiments and aspects thereof are described and illustrated in conjunction with systems, tools and methods which are meant to be exemplary and illustrative, not limiting in scope.

There is provided, in an embodiment, a method of utilizing a blind or visually impaired assistance apparatus. When, in an embodiment, combing the entire outcome data gathered from all the system's sensors (distance, camera or other means) and analyzing them and transmitting the processed data results in stereophonic sounds (so that it represents distance and direction to objects), so the person who uses the system could understand his surroundings.

There is provided, in an embodiment, a method of using the stereophonic sounding for the purposes of giving direction to the object based on the delay of sound between right ear and left ear and distance by, in some embodiments, as the intensity of the sound volume (closer objects is represented by higher volume sounds) or by, in some embodiments, as the periodicity of periodic sounds (closer objects is represented by shorter period of periodic sounds) or by, in some embodiments, as the frequency of sounds (closer objects is represented by higher frequency sounds).

There is also provided, in an embodiment, the system contains an A.I algorithm which analyzes what the system's camera captures and voice transmitting the analysis to the user, so he could identify objects and read texts. If the camera captures texts, an OCR algorithm could analyze and transmit the text to the user via sound, or if the camera captures objects, the A.I analyze what is the object and transmit to the user the name of the object via voice. The A.I may in some embodiments have face recognition algorithm working upon the camera pictures.

There is also provided, in an embodiment, a wearable system which contains several distance sensors, a camera, a personal computer or device which will be a small single board or couple of boards and headsets. The sensors could be wireless which will make the design more comfortable for the user to wear.

There is provided, in an embodiment, a method of distinguishing every outcome data in a different tune and voice depends of the purpose, the distance of the item from the person and the orientation.

In some embodiments, in order to scan and gather data from different coverage areas the system contains couple of distance sensors, or to use scanning sensors which scan in mechanical or digital way. The most ideal is to use sensors who gather wide angles and that the data may be split to be process part by part.

There is further provided, in an embodiment, the algorithms that process the sensors data are orientation depended. Especially when dealing with distance sensing the orientation is critical. In some embodiments, the long distance sensor on the face of the person, which looking toward the horizon, will alert only the distance itself and the sensors which are looking towards the ground will alert only on pits and obstacles.

In some embodiments, the system could contain also inertia and accelerometer sensors and magnetic fields sensors for the purpose of alerting the user where he is, his orientation and the direction he is heading. There is further provided, in an embodiment, the system algorithm may use the orientation from the inertia, accelerometer and magnetic sensors for better covering the processing information that came from the distance and camera. The system algorithm may use the inertia, accelerometer and magnetic sensors, in some embodiments, for step counter for distance measuring.

There is also provided, in an embodiment, the aiming direction information of sensors is crucial for giving the right interpretation and in order to better process the information from sensors.

In addition the exemplary aspects and embodiments described above, further aspects and embodiments will become apparent by study of the following detailed description.

EMBODIMENTS

1. A system for processing scenario-based information concerning an environment of a sight-disabled user, the system comprising:
   a. a plurality of sensors configured to gather the information and transfer environmental data associated with said information to a processor;
   b. a processor adapted to receive said environmental data and to output sound data; and
   c. a portable communication device associated with the sight-disabled user, said device adapted to receive said sound data from said processor, associated with said environmental data, and wherein said device is adapted to convert the sound data into brain-interpretable sound for the sight-disabled user to provide him/her with a real-time understanding of said environment.

2. The system according to embodiment 1, wherein said portable communication device outputs scenario-based stereophonic sounds to represent distance and direction from objects in a vicinity of said user, thereby enabling the user to navigate his environment.

3. The system according to embodiment 2, wherein said the stereophonic sounds provide said user with information relating to a distance and direction from the object, based on a delay of sound between a right ear and a left ear of said user.

4. The system according to embodiment 2, wherein said device is configured to adjust the volume of said stereophonic sounds, responsive to said distance.

5. A method for processing scenario-based information concerning an environment of a sight-disabled user, the method comprising:
   a. gathering information and environmental data from sensors on a user device, said data associated with objects in a vicinity of the user;
   b. processing said information using scenario-based algorithms and data to output associated sound data; and
   c. converting said sound data associated with said environmental data into scenario-based brain-interpretable sound for the sight-disabled user to provide him/her with a real-time understanding of said environment.

6. The method according to embodiment 5, wherein said converting step outputs stereophonic sounds to represent distance and direction from objects in a vicinity of said user, thereby enabling the user to navigate his/her environment.

7. The method according to embodiment 6, wherein said the stereophonic sounds provide said user with scenario-based information relating to a distance and direction from at least one of the objects, based on a delay of sound between a right ear and a left ear of said user.

8. The method according to embodiment 7, wherein said device is configured to adjust the volume of said scenario-based stereophonic sounds, responsive to said distance.

9. The method of embodiment 8, wherein said scenario-based stereophonic sounds provide direction to the at least one object based on a delay of sound between a right ear and a left ear of said user and an indication of distance by a periodicity of periodic sounds, wherein closer objects are represented by shorter period of periodic sounds.

10. The method of embodiment 9, wherein said scenario-based stereophonic sounds provide a direction to the at least one object, based on the delay of sound between right ear and left ear and distance by the frequency of sounds, wherein closer objects are represented by higher frequency sounds.

11. The method of embodiment 5, wherein said scenario-based algorithms further outputting voice-read texts, by implementing an optical character recognition (OCR) algorithm.
12. The method of embodiment 11, wherein said OCR information is from a camera on a personal device of the user and wherein said camera is used for OCR and further for playback texts in the vicinity of said user.
13. The method of embodiment 12, wherein said the scenario-based algorithms combine voice identification of objects by using an artificial intelligence (A.I.) algorithm disposed on the personal device.
14. The method of embodiment 13, wherein said information from the camera is used to identify objects by the A.I and playback the names of the objects that are in said vicinity.
15. The method of embodiment 14, wherein said A.I scenario-based algorithm comprises a face recognition algorithm, adapted to work on images captured by said camera.
16. The method of embodiment 5, wherein said information from different directions or purposes is outputted by different voices and tunes so that the user is able to identify and distinguish between information from different directions and/or sources.
17. The method of embodiment 16, wherein said scenario-based algorithms that process the sensors data are orientation dependent.
18. The method of embodiment 7, wherein said gathering step comprises at least one of:
    a. gathering data from different coverage areas;
    b. employing scanning sensors which scan in mechanical or digital ways; and
    c. using sensors which scope wide angles and gather that the data, which maybe split to be processed part by part.
19. The method of embodiment 5, wherein said information from each sensor is processed differently, based on scenario and the sensor direction or placement.
20. The method of embodiment 19, further comprising providing an alert to said user if there is a pit or an obstacle in said vicinity.
21. The system of embodiment 1, wherein said system is wearable and comprises wireless sensors, thereby making the system comfortable for the user to wear.
22. The system of embodiment 21, wherein all said sensors are connected to a main computer or a device.
23. The system of embodiment 21, wherein said system comprises wireless headsets rendering a design thereof comfortable for the user to wear.
24. The system of embodiment 23, wherein said wireless headsets are connected to a main computer or a device which the user carries.
25. The method of embodiment 5, wherein said scenario-based algorithms fuse all the data gathered from all the sensors (direction sensors, camera, GPS, navigation sensors—accelerometers, magnetic sensors) and transmit it as stereophonic sounds to said user so that it represents distance and direction to objects in different tunes and voices.
26. The method of embodiment 5, wherein said sensors comprise acceleration sensors to interpret motion information of the user and the orientation of the user in his surroundings
27. The method of embodiment 26, wherein said motion information is used for navigation purposes.
28. The system of embodiment 1, wherein said system comprises GPS for navigating the user outside and giving him directions to his destination.
29. The system of embodiment 28, wherein said system further comprises a navigation application for navigating inside a building, which uses a camera to identify scenario-based differences between images and by machine learning, the system is configured to map the insides of the building and to direct the user.
30. The system of embodiment 29, wherein said the pictures taken from the camera are scenario-based analyzed by the A.I to understand if the person is indoors or outdoors, wherein if the A.I recognizes from the camera's pictures couple of light sources and items that are usually indoors, the system understands that the person is indoors and would apply the application that navigates inside buildings, and if the camera captures the sun and items like street lights and by the usage of GPS, the system understands that it navigates outdoor and use GPS or other outdoor navigation application to navigate the user.
31. The system of embodiment 29, wherein said the system uses echo and noise cancellation so that the system removes sounds that are identified as noises and the user may get the surround sound information clearly.
32. A system comprising at least one hardware processor; and a non-transitory computer-readable storage medium having scenario-based program code embodied therewith, the program code executable by said at least one hardware processor to perform the scenario-based method of any one of embodiments 5-20 or 25-27.
    a. A system comprising at least one hardware processor; and a non-transitory computer-readable storage medium having at least two parts software; The scenario identification selection. The scenarios may be depicted by any method comprising:
        i. Intervention or commands from the user.
        ii. Policy derived selection.
    b. Context derived by AI decision based on the data that are collected from sensors. The Implementation component of algorithms or apps that make an implementation of a scenario-based program, the program code executable by said at least one hardware processor to perform the scenario-based method of any one of embodiments 5-20 or 25-27.
33. A computer program product comprising a non-transitory computer-readable storage medium having scenario-based program code embodied therewith, the program code executable by at least one hardware processor to perform the scenario-based method of any one of embodiments 5-20 or 25-27.
    a. A computer program product comprising having at least two parts software; The scenario identification selection. The scenarios may be depicted by any method comprising:
        i. Intervention or commands from the user.
        ii. Policy derived selection.
        iii. Context derived by AI decision based on the data that are collected from sensors.
    b. The Implementation component of algorithms or apps that make an implementation of a scenario-based program, the program code executable by said at least one hardware processor to perform the scenario-based method of any one of embodiments 5-20 or 25-27.

c.

The present invention will be more fully understood from the following detailed description of the preferred embodiments thereof, taken together with the drawings.

BRIEF DESCRIPTION OF THE DRAWINGS

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a simplified schematic illustration showing a system for processing three-dimensional position data of objects into scenario-based brain-interpretable sound, in accordance with an embodiment of the present invention;

FIG. 2 is a simplified schematic illustration of a scenario management component method, in accordance with an embodiment of the present invention;

FIG. 3A is a simplified schematic illustration of a scenario identification component method, in accordance with an embodiment of the present invention;

FIG. 3B is a simplified schematic illustration of an implementation component method, in accordance with an embodiment of the present invention;

FIG. 4 is a simplified schematic illustration showing a mobile communication device for processing three-dimensional position data of objects into scenario-based brain-interpretable sound, in accordance with an embodiment of the present invention;

FIG. 5 is a simplified flow chart of a method for processing three-dimensional position data of objects into scenario-based brain-interpretable sound, in accordance with an embodiment of the present invention; and FIG. 6 is a simplified flow chart of a method for providing scenario-related information in brain-interpretable sound, in accordance with an embodiment of the present invention.

In all the figures similar reference numerals identify similar parts.

DETAILED DESCRIPTION OF THE EMBODIMENTS

In the detailed description, numerous specific details are set forth in order to provide a thorough understanding of the invention. However, it will be understood by those skilled in the art that these are specific embodiments and that the present invention may be practiced also in different ways that embody the characterizing features of the invention as described and claimed herein.

Figure 1:
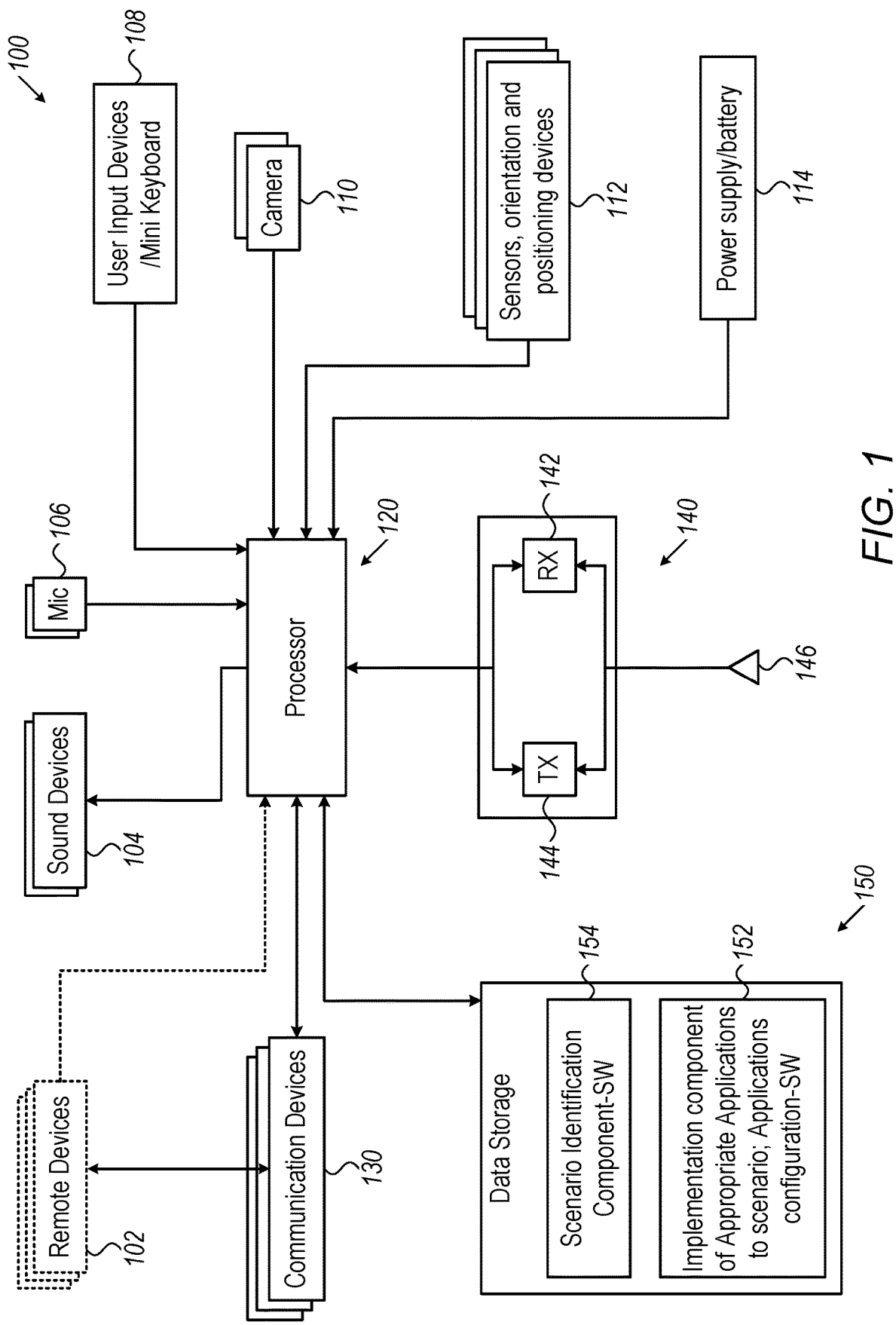

Reference is now made to FIG. 1, which is a simplified schematic illustration showing a system [100] for processing three-dimensional position data of objects into scenario-based brain-interpretable sound, in accordance with an embodiment of the present invention.

System [100] may be any dedicated computing platform or a Commercial off-the-shelf (COTS) computing platform such as cell phones, single-board computer (SBC) like Raspberry Pi platforms, PC104 computers and other computing platforms such as netbooks/laptops computers and so on. The system described in the figure includes optional connections to connect to Remote Devices [102] that may be used as a part of the system [100] and even used as integral parts of it. The Remote Devices may be connected to the system via wires such as cables (dashed line) or via wireless connections. In such case the connection is through Communication Devices [130] that serve as ports for other devices to connect to the system.

The Remote Devices may be remote headphones, speakers, mic, remote input devices such as keyboards, remote sensors like distance measuring sensors such as ultrasonic distance metering, triangulation distance measuring—such as stereoscopic cameras and Lidar, orientation sensors like compass sensors, acceleration sensors, cameras and positioning devices such as GPS.

The system comprises Sound devices [104] that are integrated to the system or as part of the Remote Devices. Such Sound devices may be speakers or headphones. The Sound devices may be stereo Sound devices. The Sound devices serve to give the user information about his surrounding via sound. The system comprises Mic devices [106] that are integrated to the system or as part of the Remote Devices. The mic devices may be used as an input device for sound commands and other sound data from the user; may be inserted or recorded to the OS or applications to work on or to be process further. Sound that are captured by the mic devices may use as echo and noise cancelation so that the system removes sounds that are identified as noises and the user may get the surround sound information clearly. The mic devices may be used by the OS or the Scenario Identification Component SW to understand the Scenario that the user is involved in.

The system comprises User Input Devices/Mini Keyboard [108] that are integrated to the system or as part of the Remote Devices. The Input Devices/Mini Keyboard may serve as an input device that commands and other data that the user wants to give to the OS or the applications that run on the system is transfer into. The input devices may be also cameras that may extract and process the user gestures for input commands.

The system comprises cameras [110] that are integrated to the system or as part of the Remote Devices. Cameras serve as input devices that insert visual data into the system so that the OS or applications may extract and process the visual information and make the data fitting according scenarios that are processed by the system. As part of the scenarios user gestures for input commands may be processed. As part of the scenarios the Scenario Identification Component—SW may use the information from the cameras to decide which scenario is fit for a specific moment or situation.

The system comprises sensors, orientation and positioning devices [112] that are integrated to the system or as part of the Remote Devices. The sensors, orientation and positioning devices are sensors like distance measuring sensors such as ultrasonic distance metering, triangulation distance measuring—such as stereoscopic cameras and Lidar, orientation sensors like compass sensors, acceleration sensors, cameras and positioning devices such as GPS. These sensors collect data that are fused together by the OS and applications that are running as an implementation of scenario configuration. The system comprises Power supply/battery [114] that is integrated to the system to be able the system to operate as a standalone mobile device. The system comprises a processor or processors [120] that integrated to the system and used to run all the required algorithms. The processor may be x86 type or ARM based or any RISK processor, it may be ab FPGA or system on a chip (SOC). It may be connected to additional accelerators such as HW, FPGAs, GPUs etc'. The processor wills activate the software (SW) that is stored in the data storage [150] and run the algorithms as an application or as an operating system (OS) that run applications and so on.

The processor is configured to run the software part that is Scenario Identification Component—SW and the software part that is Implementation component of Appropriate Applications to scenario; Applications configuration—SW. The system comprises Communication Devices [130] that are integrated to the system to be served as ports for other devices to connect to the system and to import or export data from other modules. The need for to import or export data from other modules is for operation of the OS and application according to his requirements. That includes software Applications updates including the OS or getting new store Applications or transfer required data. The system may have standard wireless Communication Devices [140] such as cellular modules, WiFi modules and so on that are integrated to the system to be served as ports for other devices to connect to the system and to import or export data from other places.

These modules are expansion of the Communication Devices noted above that may be non-common or non-standard. The standard wireless communication devices have antennas [146], transmission modules (TX) [144] and receiving modules (RX) [142]. The system comprises data storage [150] that is integrated to the system and used to store the algorithms as an application or as an OS and application software that is need for the operation of the system and so on.

The data storage saves the software part that is Scenario Identification Component—SW [154] and the software part that is Implementation component of Appropriate Applications to scenario; Applications configuration—SW [152]. That is needed in order to run the system adequate to scenario-based situations. The Scenario Identification Component—SW [154] is software whose purpose is to decide either by policy based on data that are collected from sensors or by user intervention or commands which is Scenario Identity to be operate at the specific situation. This software may be a part of the OS of the system or as a part of the main application of the system.

A scenario is a proper situation and purpose that a blind or visually impaired user is stand in front of. For example, if a blind or visually impaired users intent is to walk in a street to navigate safely to a specific end point destination, then a GPS navigation SW with voice direction commands with data from GPS module may be operate with distance sensors like Lidar or ultrasonic distance sensors combining data from cameras to identify sidewalk routes with AI SW to insure that a blind or visually impaired person walks according the routes of the sidewalk. When reaching to cross a road, the AI detects a road ahead and notifies the blind or visually impaired person. The scenario is changed to a road crossing scenario when the AI detects cars, traffic lights on which give verbally the color of the traffic lights and notifying when start and stop the car roads and if the cars respond and stops. All this is accompanied with compass and acceleration meters in order to validate course and even read street signs. Another scenario is the situation when a blind or visually impaired user gets inside a building then the navigation by GPS ends and relay on AI that detects lamp lights and other not moving reference points that are fuse with data from compass, altimeter and acceleration sensors to measure the location.

With AI, identification is made of doors and elevators and walls to guide a blind or visually impaired user to his destination in the building. When getting into elevator the system need to identify it and go to an elevator scenario, the AI camera needs to identify the elevator doors if open or close and where is the elevator command panel, the numbers of the buttons that the user is aiming and read it, identified the floor number and notify verbally and so on. Another example of situation is when a blind or visually impaired user is walking near a pool, the surface of water seems to a distance sensor like Lidar and ultrasonic as a floor, but the AI camera may detect the edge of the pool and may notify upon the danger.

Another example of scenario is when a blind or visually impaired person cooks a stew. A blind or visually impaired person put some groceries on a table and the system gives instructions to a blind or visually impaired person upon each component its identification and location on a table.

Based on that Scenario the software part that is Implementation component of Appropriate Applications to scenario; Applications configuration—SW [152] makes a configuration of algorithms or sub scenario applications to run as a full configuration. The configuration of apps and algorithms serves according the scenario, when the sensors collect data that are fused together by the OS and applications that are running as an implementation of scenario configuration.

Figure 2:
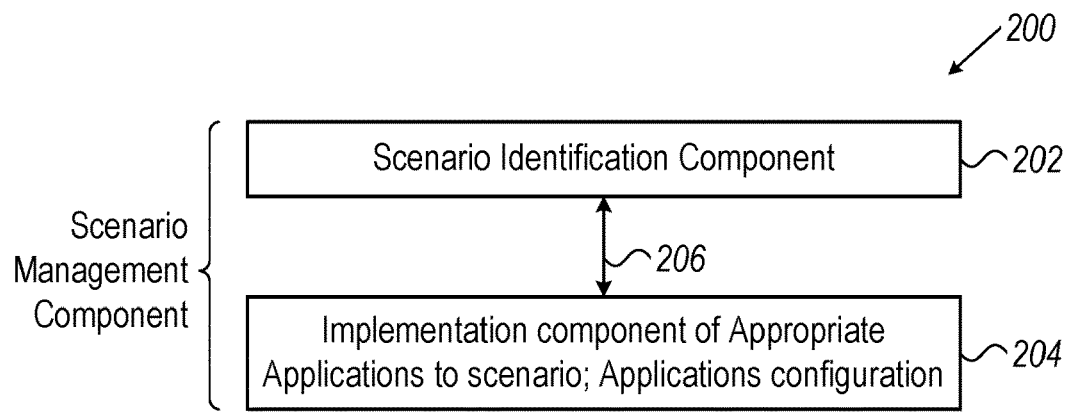

Turning to FIG. 2, there is seen a simplified schematic illustration of a scenario management component method [200], in accordance with an embodiment of the present invention.

The method comprises an algorithm for repeatedly updating the user with scenario identification information/data from a scenario identification component [202] and providing the user with specific Apps from an App choosing component [204], in accordance with the specific scenario, in which the user is currently found.

This method is function as to manage and orchestrate a Scenario based operation of a system.

A scenario is a proper situation and purpose that a blind or visually impaired user is stand in front of. For example, if a blind or visually impaired user's intent is to walk in a street to navigate safely to a specific end point destination, then a GPS navigation SW with voice direction commands with data from GPS module may be operate with distance sensors like Lidar or ultrasonic distance sensors combining data from cameras to identify sidewalk routes with AI SW to insure that a blind or visually impaired person walks according the routes of the sidewalk.

When reaching to cross a road, the AI detects a road ahead and notify the blind or visually impaired person. The scenario is changed to a road crossing scenario when the AI detects cars, traffic lights on which give verbally the color of the traffic lights and notifying when start and stop the car roads and if the cars respond and stops. All this is accompanied with compass and acceleration meters in order to validate course and even read street signs.

Another scenario is the situation when a blind or visually impaired user gets inside a building then the navigation by GPS ends and relay on AI that detects lamp lights and other not moving reference points that are fuse with data from compass, altimeter and acceleration sensors to measure the location.

With AI, identification is made of doors and elevators and walls to guide a blind or visually impaired user to his destination in the building. When getting into elevator the system need to identify it and go to an elevator scenario, the AI camera needs to identify the elevator doors if open or close and where is the elevator command panel, the numbers of the buttons that the user is aiming and read it, identified the floor number and notify verbally and so on. Another example of situation is when a blind or visually impaired user is walking near a pool, the surface of water seems to a distance sensor like Lidar and ultrasonic as a floor, but the AI camera may detect the edge of the pool and may notify upon the danger.

Another example of scenario is when a blind or visually impaired person cooks a stew. A blind or visually impaired person put some groceries on a table and the system gives instructions to a blind or visually impaired person upon each component its identification and location on a table.

The Scenario Management Component has two parts (algorithms) minimum.

The first part is the Scenario Identification Component [202] that is software that its purpose is to decide either by policy based on data that are collected from sensors or by user intervention or commands, which Scenario Identity to be operated at a specific situation. This software may be a part of the OS of the system or as a part of the main application of the system. Based on that Scenario, the second part is the Implementation component of Appropriate Applications to scenario; Applications configuration [204] that makes a configuration of algorithms or sub scenario applications to run as a full configuration. The configuration of apps and algorithms serves according the scenario, when the sensors collect data that are fused together by the OS and applications that are running as an implementation of scenario configuration. Although the Scenario Identification Component [202] is the dominate and decides for the Implementation component of Appropriate Applications to scenario; Applications configuration [204] which scenario upon to make an apps configuration, the connection between them is bi-directional [206] since recommendations upon next scenario situation based on the sensors data that are collected at a specific configuration that fused and AI analyzed according the scenario that is implemented, is transfer back to the Scenario Identification Component in order to adequate the scenario to a specified situation.

Figure 3A:
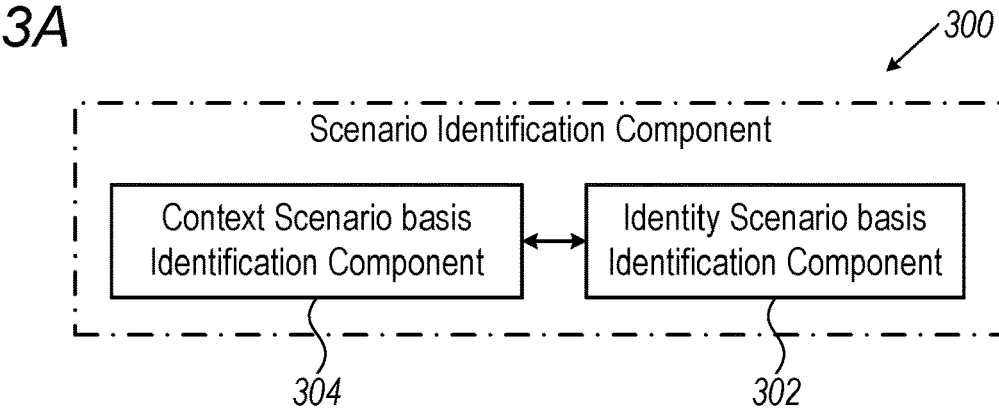

Reference is now made to FIG. 3A, which is a simplified schematic illustration of a scenario identification component method [300], in accordance with an embodiment of the present invention.

The method comprises both an algorithm or component for context scenario identification [304] and an algorithm or component [302] for scenario decision making, based on the identity of the user. The two components/algorithms update each other, to output the optimized selection of Apps or only one App for the specific user, based on criteria reflecting the user's identity and the context of the specific real-time scenario.

FIG. 3A: More detailed description of the option parts of the Scenario Identification Component [300].

The Scenario Identification Component may operate based on Identity Scenario basis Identification Component [302]. In this case, it is based on a command from the user, which is inserted via an input device such as keyboards, or gestures that are captured by camera or by voice commands, that a specific scenario identity is provided according to which they operate.

The Scenario Identification Component is operative to be based on a Context Scenario basis Identification Component [304]. In this case recommendations upon next scenario situation based on the sensors data that are collected at a specific configuration that fused and AI analyzed according the scenario that is implemented, are transferred back from the Implementation component of Appropriate Applications to scenario; Applications configuration [350] to the Context Scenario basis Identification Component [304] in order to adequate the scenario to a specified situation.

It is obvious that the two methods of Scenario identification may operate in parallel or in any combination between them according the Scenario Management Component application algorithm.

Figure 3B:
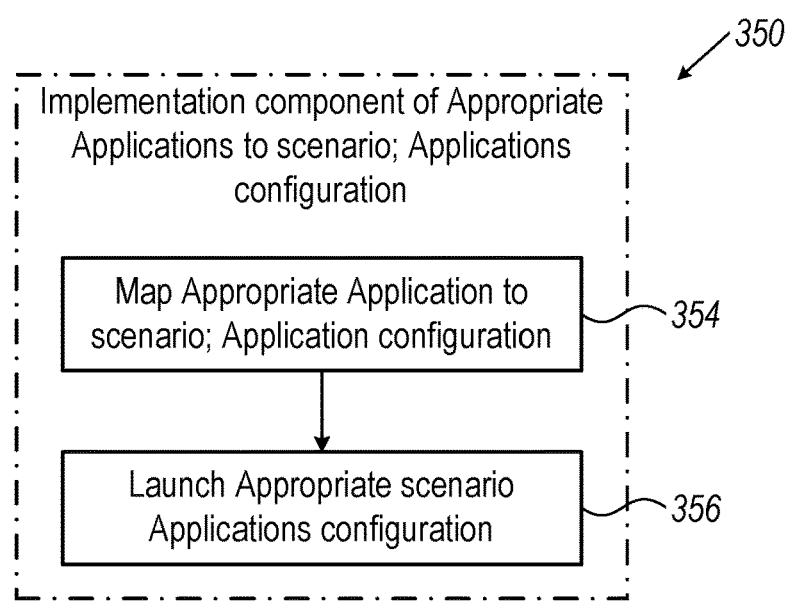

FIG. 3B shows a simplified schematic illustration of an implementation component method [350], in accordance with an embodiment of the present invention.

FIG. 3B: More detailed description of the option parts of the Implementation component of Appropriate Applications to scenario; Applications configuration [350].

This part includes two sub parts. The first part is the algorithm for Mapping Appropriate Applications to scenario; Applications configuration [354]. This part makes a list of algorithms/apps that needs to run together in order to execute a specific scenario configuration. The second part is the Launch Appropriate scenario Applications configuration [356] that executes the apps/algorithms that are needed according the list that the Map Appropriate Applications to scenario; Applications configuration [354] has made and connect them to operate together via an envelope algorithm/app to be functioning according the desired scenario.

Figure 4:
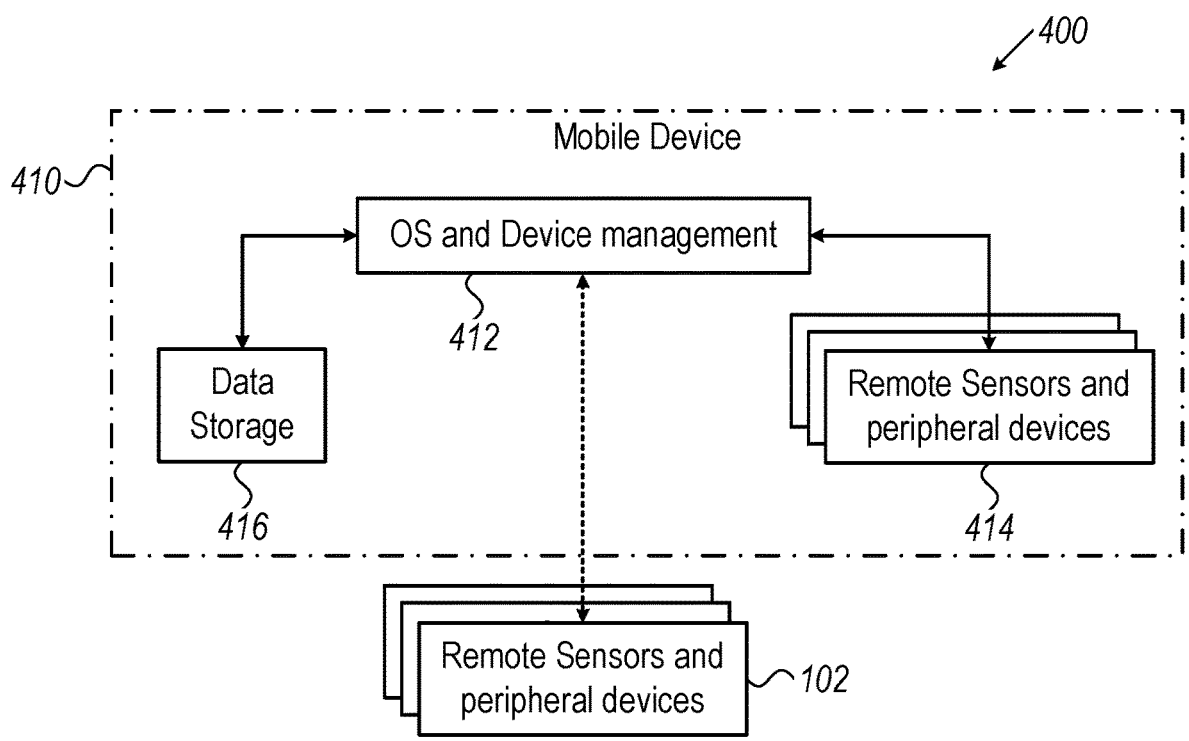

Reference is now made to FIG. 4, which is a simplified schematic illustration showing a mobile communication device [400] for processing three-dimensional position data of objects into scenario-based brain-interpretable sound, in accordance with an embodiment of the present invention. The mobile device receives data from the system ([100], not shown) and/or from remote sensors and peripheral devices [102] (as described hereinabove).

The mobile device [130] comprises and operating system and device management unit [412], constructed and configured to receive and provide data to a data storage unit [416]. The management unit [412] is further configured to provide and receive data from remote sensors and peripheral devices such as stereoscopic cameras and Lidar, orientation sensors like compass sensors, acceleration sensors, cameras and positioning devices such as GPS [414]. For example, the mobile device receives data about objects surrounding the user and is operative to translate the data into a series of different sounds, musical tones or noises, which the user's brain may interpret to provide the user with a picture of the objects in his/her surroundings.

FIG. 4: A high-level mobile device system [400] description (see in more details FIG. 1).

This mobile device [410] may be any dedicated computing platform or a Commercial off-the-shelf (COTS) computing platform such as cell phones, single-board computer (SBC) like Raspberry Pi platforms, PC104 computers and other computing platforms such as netbooks/laptops computers and so on. The system described in the figure includes optional outside system Remote Sensors and peripheral devices [102] that may be used as part of the system [400] and even used as integral parts of it.

The Remote Sensors and peripheral devices may be connected to the system (dashed line) via wires such as cables or via wireless connections. The mobile device [410] may use integral Remote Sensors and peripheral devices

[414] that are part of the device itself. The Remote Sensors and peripheral devices may be remote headphones, speakers, mic, remote input devices such as keyboards, remote sensors like distance measuring sensors such as ultrasonic distance metering, triangulation distance measuring—such as stereoscopic cameras and Lidar, orientation sensors like compass sensors, acceleration sensors, cameras and positioning devices such as GPS.

The Data Storage [416] stores the software part that needs to run the system. The OS and Device management [412] is the management algorithms that run the device, use the data from the Sensors and peripheral devices and also use apps and algorithms that are stored in the data storage [416] to run the system adequate to scenario-based situations.

A scenario is a proper situation and purpose that a blind or visually impaired user is stand in front of. For example, if a blind or visually impaired user's intent is to walk in a street to navigate safely to a specific end point destination, then a GPS navigation SW with voice direction commands with data from GPS module may be operate with distance sensors like Lidar or ultrasonic distance sensors combining data from cameras to identify sidewalk routes with AI SW to insure that a blind or visually impaired person walks according the routes of the sidewalk.

When reaching to cross a road, the AI detects a road ahead and notify the blind or visually impaired person. The scenario is changed to a road crossing scenario when the AI detects cars, traffic lights on which give verbally the color of the traffic lights and notifying when start and stop the car roads and if the cars respond and stops. All this is accompanied with compass and acceleration meters in order to validate course and even read street signs.

Another scenario is the situation when a blind or visually impaired user gets inside a building then the navigation by GPS ends and relay on AI that detects lamp lights and other not moving reference points that are fuse with data from compass, altimeter and acceleration sensors to measure the location. With AI identification of doors and elevators and walls, the method is operative to guide a blind or visually impaired user to his destination in the building.

When getting into elevator the system need to identify it and go to an elevator scenario, the AI camera needs to identify the elevator doors if open or close and where is the elevator command panel, the numbers of the buttons that the user is aiming and read it, identified the floor number and notify verbally and so on. Another example of situation is when a blind or visually impaired user is walking near a pool, the surface of water seems to a distance sensor like Lidar and ultrasonic as a floor, but the AI camera may detect the edge of the pool and may notify upon the danger.

Another example of scenario is when a blind or visually impaired person cooks a stew. A blind or visually impaired person put some groceries on a table and the system gives instructions to a blind or visually impaired person upon each component its identification and location on a table.

Figure 5:
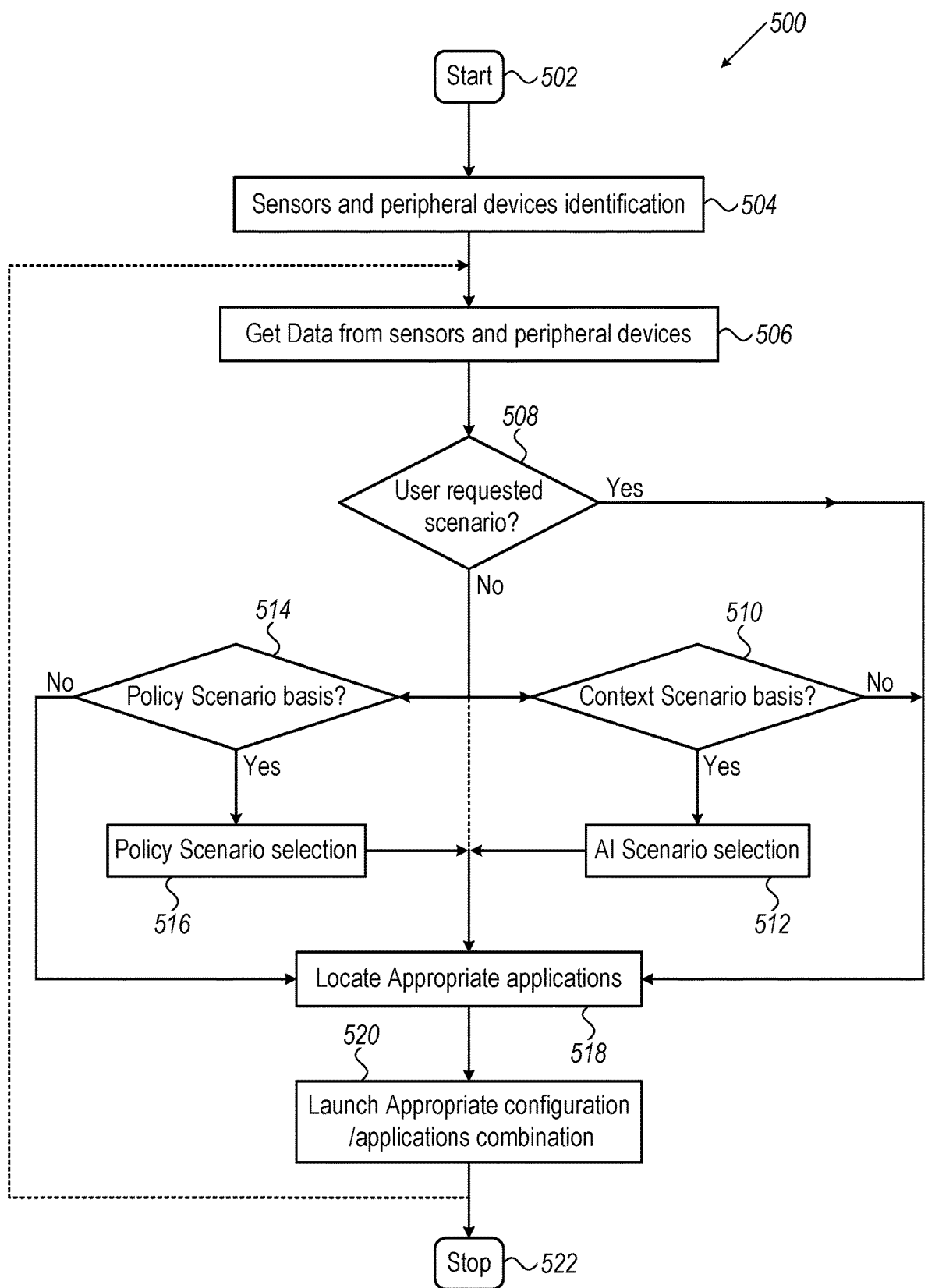

Reference is now made to FIG. 5, which is a simplified flow chart of a method [500] for processing three-dimensional position data of objects into scenario-based brain-interpretable sound, in accordance with an embodiment of the present invention.

Without loss of generality, the figures describe in a more details possible algorithm for handling the tasks of the OS and Device management Component [412] in mobile device [410] that is described in FIG. 4.

The figure describes in a more detail a possible algorithm for handling the tasks of the OS and Device management Component [500].

The algorithm starts with the Start [502] initiation step when a user turns on the device. Then it proceeds to a Sensors and peripheral devices identification [504] step when it checks and recognizes all the sensors and peripheral devices that are attached to the device or embed in it. The next step is Get Data from sensors and peripheral devices [506] when the algorithm receives data from the sensors and peripheral devices to be analyzed. Then there is a decision task which comprises a user requested scenario decision step [508], in which it decides if a chosen scenario is based on Context or Policy. If the answer for the question is "yes" and a specific command is received either by a voice command or a gesture or from a keyboard or other means then it proceeds to Locate Appropriate applications step [518] and make a list of the apps or algorithms that are needed to run the specific scenario.

The next step is to run the step of Launch Appropriate configuration/applications combination step [520] that executes the apps/algorithms that are needed according the list that the Locate Appropriate applications step [518] has made and connect them to operate together via an envelope algorithm/app to be functioning according the desired scenario.

A scenario is a proper situation and purpose that a blind or visually impaired user is stand in front of. For example, if a blind or visually impaired users intent is to walk in a street to navigate safely to a specific end point destination, then a GPS navigation SW with voice direction commands with data from GPS module may be operate with distance sensors like Lidar or ultrasonic distance sensors combining data from cameras to identify sidewalk routes with AI SW to insure that a blind or visually impaired person walks according the routes of the sidewalk. When reaching to cross a road, the AI detects a road ahead and notifies the blind or visually impaired person. The scenario is changed to a road crossing scenario when the AI detects cars, traffic lights on which give verbally the color of the traffic lights and notifying when start and stop the car roads and if the cars respond and stops. All this is accompanied with compass and acceleration meters in order to validate course and even read street signs.

Another scenario is the situation when a blind or visually impaired user gets inside a building then the navigation by GPS ends and relay on AI that detects lamp lights and other not moving reference points that are fuse with data from compass, altimeter and acceleration sensors to measure the location.

With AI, identification is performed of doors and elevators and walls, in order to guide a blind or visually impaired user to his/her destination in the building. When getting into elevator the system need to identify it and go to an elevator scenario, the AI camera needs to identify the elevator doors if open or close and where is the elevator command panel, the numbers of the buttons that the user is aiming and read it, identified the floor number and notify verbally and so on. Another example of situation is when a blind or visually impaired user is walking near a pool, the surface of water seems to a distance sensor like Lidar and ultrasonic as a floor, but the AI camera may detect the edge of the pool and may notify upon the danger.

Another example of scenario is when a blind or visually impaired person cooks a stew. A blind or visually impaired person put some groceries on a table and the system gives instructions to a blind or visually impaired person upon each component its identification and location on a table.

After launching the desired scenario configuration, the system goes back to get data from sensors and peripheral devices [506] step (dashed line) or go to Stop [522] step that is done when the user turned off the device.

In case when the "If" question of User requested scenario? [508] is "No" then it proceeds to a process of how to determine of which scenario to choose and depict. Without loss of generality it may pass several "If" questions such as Context Scenario basis? [510] when in this case, if the answer is "yes" then it goes to AI Scenario selection [512] step that makes recommendations upon next scenario situation based on the sensors data that were collected from the Get Data from sensors and peripheral devices [506] step, that fused and AI analyzed in order to adequate the scenario to a specified situation.

Then, the chosen scenario is transferred to the Locate Appropriate applications [518] step. If the answer is "No" one may do a loop that transfer it to the next decision "If" question in the scenario depicting process. In this figure scheme we choose without loss of generality to use the loop-back from Launch Appropriate configuration/applications combination [520] step to Get Data from sensors and peripheral devices [506] step (dashed line) that already described and therefore we past the decision to Locate Appropriate applications [518] step that in this case pass a "Null" scenario to Locate Appropriate applications [518] step that is "null" (do nothing) and goes back with the loop.

If the "If" question is based on a Policy Scenario basis? [514] and the answer is "Yes" then it goes to Policy Scenario selection [516] step when depend on policy scheme the scenario is chosen and transferred to the Locate Appropriate applications [518] step. If "No" is given to the "If" question, then it passes a "Null" scenario to Locate Appropriate applications [518] step and the loop continues (dashed line) until covering all possible scenario driving "If" processes.

Figure 6:
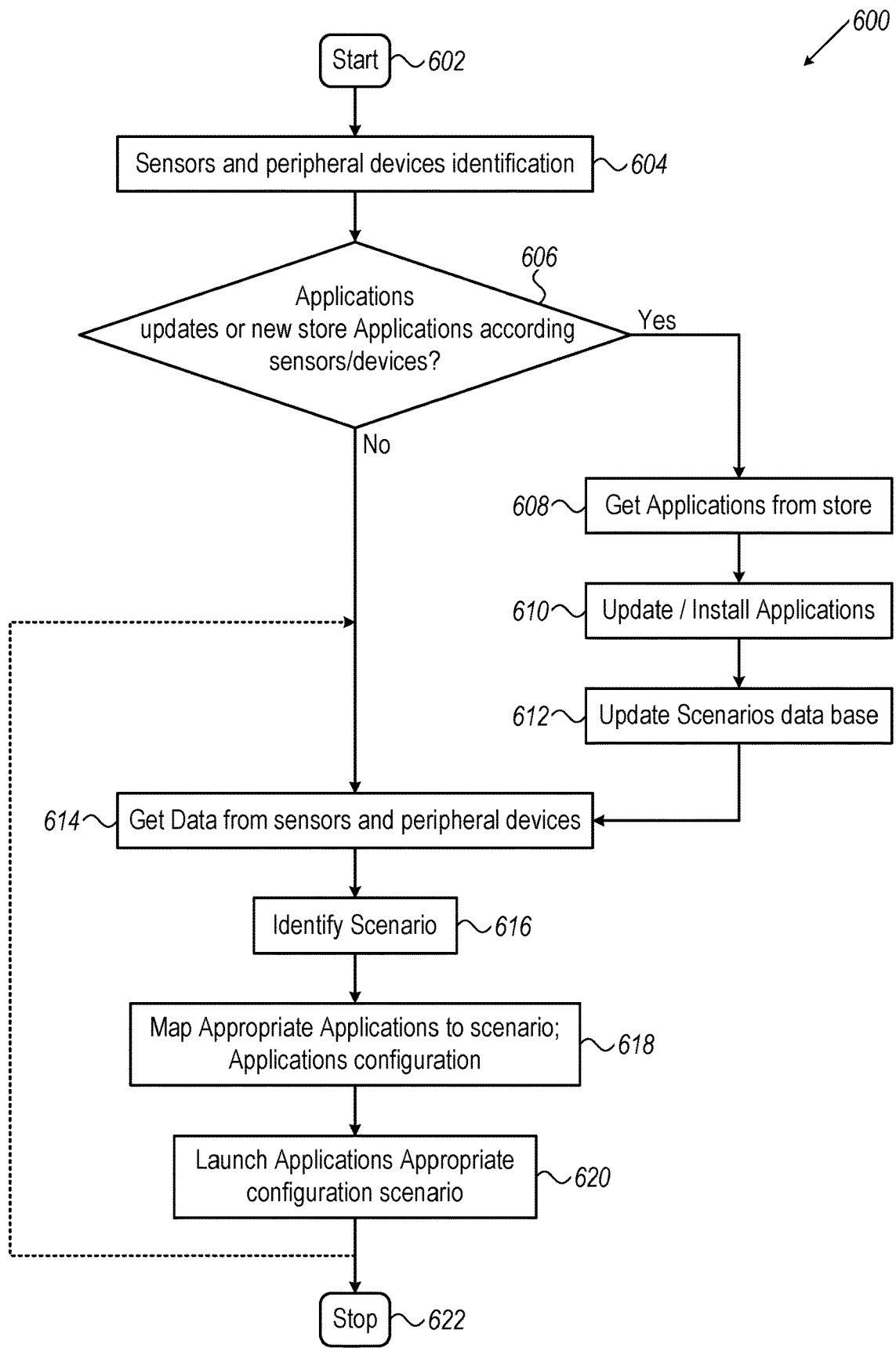

Reference is now made to FIG. 6, which is a simplified flow chart of a method [600], for providing scenario-related information in brain-interpretable sound, in accordance with an embodiment of the present invention.

The figure describes in a more detail a possible algorithm for handling the tasks of the OS and Device management Component [600].

The algorithm starts with the Start [602] initiation step when a user turns on the device.

Then it proceeds to a Sensors and peripheral devices identification [604] step when it checks and recognizes all the sensors and peripheral devices that are attached to the device or embed in it. Next, there is "If" function: Applications updates or new store Applications according sensors/devices? [606] that check if there are new algorithms/apps, which are benefit to a blind or visually impaired user, that the OS and Device management Component [600] may use.

If the answer is "Yes" then we start a process of updating the software packages. In this process we start with operation Get Applications from store [608] to download the SW packages that need to be installed. Next, Update/Install Applications [610] is executed and the new SW packages are installed.

The next step after installing the SW packages is Update Scenarios data base [612] that updates the instructions of Identify Scenario [616] and Map Appropriate Applications to scenario; Applications configuration [618] so that the overall OS and Device management Component [600] are upgraded. After updating the overall OS and Device management Component [600] we go to the ordinary/standard step of operation of the overall OS and Device management Component [600].

This ordinary/standard step of operation starts with Get Data from sensors and peripheral devices [614] when the algorithm receives data from the sensors and peripheral devices to be analyzed. In case that the answer for the "If" question in Applications updates or new store Applications according sensors/devices? [606] is "No" we go directly to the ordinary/standard step of operation start with Get Data from sensors and peripheral devices [614]. Next, we go to the step of Identify Scenario [616] when an identification of an appropriate scenario to a situation based on the data that received from sensors and peripheral devices [614], the instructions for scenario identification in database and an AI processing.

A scenario is a proper situation and purpose that a blind or visually impaired user is stand in front of. For example, if a blind or visually impaired users intent is to walk in a street to navigate safely to a specific end point destination, then a GPS navigation SW with voice direction commands with data from GPS module may be operate with distance sensors like Lidar or ultrasonic distance sensors combining data from cameras to identify sidewalk routes with AI SW to insure that a blind or visually impaired person walks according the routes of the sidewalk.

When reaching to cross a road, the AI detects a road ahead and notify the blind or visually impaired person. The scenario is changed to a road crossing scenario when the AI detects cars, traffic lights on which give verbally the color of the traffic lights and notifying when start and stop the car roads and if the cars respond and stops. All this is accompanied with compass and acceleration meters in order to validate course and even read street signs.

Another scenario is the situation when a blind or visually impaired user gets inside a building, then the navigation by GPS ends and relay on AI that detects lamp lights and other not moving reference points that are fuse with data from compass, altimeter and acceleration sensors to measure the location.

With AI, identification is made of doors and elevators and walls to guide a blind or visually impaired user to his/her destination in the building. When getting into elevator the system need to identify it and go to an elevator scenario, the AI camera needs to identify the elevator doors if open or close and where is the elevator command panel, the numbers of the buttons that the user is aiming and read it, identified the floor number and notify verbally and so on. Another example of situation is when a blind or visually impaired user is walking near a pool, the surface of water seems to a distance sensor like Lidar and ultrasonic as a floor, but the AI camera may detect the edge of the pool and may notify upon the danger.

Another example of scenario is when a blind or visually impaired person cooks a stew. A blind or visually impaired person put some groceries on a table and the system gives instructions to a blind or visually impaired person upon each component its identification and location on a table.

A next step is a Map Appropriate Applications to scenario; Applications configuration [618], that makes a list of the apps or algorithms that are needed to run the specific scenario. The next step is to run the step of Launch Appropriate scenario Applications configuration [620] that executes the apps/algorithms that are needed according the list that the Map Appropriate Applications to scenario; Applications configuration [618] step has made and connect them to operate together via an envelope algorithm/app to be functioning according the desired scenario.

After launching the desired scenario configuration, the system goes back to get data from sensors and peripheral devices [614] step (dashed line) or go to Stop [622] step that is done when the user turned off the device.

Disclosed herein are system method, computer program product or hardware product and A.I for helping blind and visually impaired people who wear the system to cope with their environment, read texts and identify object, only with the help of the system itself.

As noted above, based on the assumption that humans' hearing is stereophonic and may distinguish between different frequencies and volumes and these capabilities are used for environment understanding by sounding, it is possible to build a wearable technological system for blind and visually impaired people to cope with the environment.

Accordingly, in some embodiments, such a system will contain several distance sensors, dedicated advanced algorithms and an A.I to scenario-based fuse the data gathered from the sensors and to transmit it by stereophonic sounding (so that it represents distance and direction to objects) to a person wearing it in a way which will allow him to understand his environment and act accordingly. In some embodiments, the stereophonic sounding will give direction to the object based on the delay of sound between right ear and left ear and distance by, in some embodiments, as the intensity of the sound volume (closer objects is represented by higher volume sounds) or by, in some embodiments, as the periodicity of periodic sounds (closer objects is represented by shorter period of periodic sounds) or by, in some embodiments, as the frequency of sounds (closer objects is represented by higher frequency sounds).

In some embodiments, in order to cover the environment, there is a need to use number of sensors to gather data from different coverage areas, or to use scanning sensors which scan in mechanical or digital way (similar usage of the walking stick the blind use). The most ideal is to use sensors who gather wide angles and that the data may be split to be process part by part (like camera that takes pictures and the picture may be split to several parts which processed separately).

In some embodiments, the method is to scenario-based analyze the information from each sensor separately at a given time and to combine all the data into stereophonic sounds (so that it represents distance and direction to objects). Every outcome data will be distinguished in a different tune and voice depends of the purpose, the distance and orientation of the item from the person. In the case of the camera the system catches every piece of picture separately and it gives it a suitable scenario-based representation with its own voice and tune.

In some embodiments, the scenario-based algorithms that process the sensors data are orientation depended. Especially when dealing with distance sensing the orientation is critical. For example, the sensor for finding an obstacle or a pit should not alert if there isn't any obstacle or a pit but at the moment it detects something, it will alert accordingly. In order to do so, a specific distance will be calibrated as the zero point and in a distance greater or shorter than it; the sensor will alert as negative or positive distance respectively. However, in some embodiments, the long distance sensor on the face of the person, which looking toward the horizon, will alert only the distance itself, when the infinite distance will be calibrate as zero and the alert will be intensive as the obstacle will be closer to the person.

In some embodiments, the system comprises a camera, so when there will be for example a pool full of water, the distance sensor may or may not alert for a pit but the A.I that process the picture from the camera will detect that the surface of water is a pool and alert the person from the falling into the pool.

In some embodiments, the system may contain wireless sensors which will make the design more comfortable for the user to wear. All the sensors will be connected to a main computer or a hardware device which the person will carry. The personal computer or device will be a small single board or couple of boards but with enough processing hardware which could run all the applications, algorithms and the A.I. The system will be wearable as glasses and belt which will contain the wireless sensors and the personal computer or processing device.

In some embodiments, the headsets may be wireless.

In some embodiments, the scenario-based algorithm will contain number of parts which each part will be analyzing different things, for example in the front camera there will be OCR analyze of text and reading it in a certain voice. One algorithm is an A.I which analyzing what the sensors are detecting, for example if the camera snap a picture of a cup or a computer mouse the A.I will detect and analyze that the object is what it is and will alert the user in a certain voice. The A.I may in some embodiments have face recognition algorithm working upon the camera pictures.

In some embodiments, different distances of different sensors, depend on the scenario, will be sound as warning sounds in a stereophonic way (so that it represents distance and direction to objects) which will notify the user what is in surround of him and will enable him to walk and cope with the environment independently.

In some embodiments, the present invention fuses up all the data from all the distance sensors and the camera together and will be scenario-based transmitted to the user in a stereophonic way (so that it represents distance and direction to objects). In some embodiments, the system could contain also inertia and accelerometer sensors and magnetic fields sensors (Hall Effect and digital compass) for the purpose of alerting the user where he is, his orientation and the direction he is heading.

In some embodiments, the present invention, the system scenario-based algorithm, may use the orientation from the inertia, accelerometer and magnetic sensors for better covering the processing information that came from the distance and camera. The system algorithm may use the inertia, accelerometer and magnetic sensors for step counter for distance measuring. All the information above, in some embodiments, may be scenario-based fused with GPS information or other navigation procedure (software or hardware), so that the system will add voice information to the GPS navigation or other navigation procedure. The system may use all the sensors for navigation inside buildings application. For example the scenario-based algorithm may take sequential camera pictures and detects the difference and changes between the sequential pictures to detect movements and fusion it with the information from odometer to count steps and also fuse it with inertia and accelerometer sensors and more (like sun recognizing and navigate due to sun position accordance the time hour) in order to get better navigation and mapping. In some embodiments, the aiming direction information of sensors is crucial for giving the right interpretation and in order to better process the information from sensors. Such as if the sensors are directing down they are for detecting pits or obstacles and on the other hand if the sensor is directing towards the horizon it is for detecting things in front of the person such as people and signs.

In some embodiments, the system comprises at least one two parts of software; one is the scenario identification selection. The scenarios may be depicted by any method comprising:

1. Intervention or commands from the user.
2. Policy derived selection.
3. Context derived by AI decision based on the data that are collected from sensors.

The second part of software is an Implementation component of algorithms or apps that make an implementation of a scenario-based program.

The present invention provides systems, methods, devices and software for improving the quality of life for blind and visually impaired people.

The system of the present invention is constructed and configured top enable blind and visually impaired people to read texts, identify objects and colors and walk and act freely as if they could see in every environment (indoors and outdoors), all at once by only the help of the system's device itself.

The device enables blind and visually impaired people to fulfill themselves and contribute to society economically and socially. The blind and visually impaired people will not be a burden because society will not have to spend on welfare and nursing for them and also the blind and visually impaired could easily enter the normal work cycle and thus increasing productivity.

The current invention relates to a system with a novel scenario-based method for processing information and data collected from sensors, transmitting the data as semi-raw data by audio to the user, in which his/her mind/brain is able to process thereby providing him/her with an understanding of the surrounding environment by "seeing via hearing". This technique enables the system to use less computer resources.

According to some embodiments of the present invention, the system uses echolocation, which is the use of sound waves to determine where objects are located in three dimension space. Due to hearing abilities, a human may detect a direction and a range from a sound source, and it is possible to identify the differences between different sounds/voices. The system contains several different types of distance sensors (ultrasonic, LIDAR etc.), camera, neural network for identifying objects and reading texts and Can-U-C's scenario-based algorithms. The system gathers data from the sensors in medium Bandwidth of dozens MBPS as video, length and location.

According to some embodiments, the system of the present invention processes the data and transmits it in analog audio in a rate up to 400 KBPS, which is equivalent to low resolution video but enough to understand the environment. It is possible to settle even in smaller bandwidths as 50 KBPS for functioning. The system encodes the information: location, speed, direction and more and scenario-based transmits it to the person in a way his mind could process it quickly and intuitively.

The present invention may be a system, a method, and/or a computer program product. The computer program product may include a computer readable storage medium (or media) having computer readable program instructions thereon for causing a processor to carry out aspects of the present invention.

The computer readable storage medium may be a tangible device that may retain and store instructions for use by an instruction execution device. The computer readable storage medium may be, for example, but is not limited to, an electronic storage device, a magnetic storage device, an optical storage device, and electromagnetic storage device, a semiconductor storage device, or any suitable combination of the foregoing. A non-exhaustive list of more computer diskette, a hard disk, a random access memory (RAM), a read only memory (ROM), an erasable programmable read only memory (EPROM or Flash memory), a static random access memory (SRAM), a portable compact disc read only memory (CD-ROM), a memory stick, a mechanically encoded device having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Rather, the computer readable storage medium is a non-transient (i.e., not-volatile) medium.

Computer readable program instructions described herein may be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, Matlab, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts. These computer readable program instructions may also be stored in a computer readable storage medium that may direct a computer, a programmable data processing apparatus, and/or other devices to function in a particular manner, such that the computer readable storage medium having instructions stored therein comprises an article of manufacture including instructions which implement aspects of the function/act.

The computer readable program instructions may also be loaded onto a computer, other programmable data processing apparatus, or other device to cause a series of operational steps to be performed on the computer, other programmable apparatus or other device to produce a computer implemented process, such that instructions which execute on the computer, other programmable apparatus, or other device implement the functions/acts.

The descriptions of the various embodiments of the present invention have been presented for the purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to the best explain the principles of the embodiments, the practical application or technical improvement over technologies found in the marketplace, or to enable others of ordinary skill in the art to understand the embodiments disclosed herein.

The references cited herein teach many principles that are applicable to the present invention. Therefore the full contents of these publications are incorporated by reference herein where appropriate for teachings of additional or alternative details, features and/or technical background.

It is to be understood that the invention is not limited in its application to the details set forth in the description contained herein or illustrated in the drawings. The invention is capable of other embodiments and of being practiced and carried out in various ways. Those skilled in the art will readily appreciate that various modifications and changes may be applied to the embodiments of the invention as hereinbefore described without departing from its scope, defined in and by the appended claims.

The invention claimed is:

1. A system for processing scenario-based information using scenario-based algorithms concerning an environment of a sight-disabled user, the system comprising:
 a plurality of sensors configured to gather the information and transfer environmental data associated with said information to a processor;
 a data storage for storing software comprising:
  a) a scenario identification component SW; and
  b) an Implementation component software of Appropriate Applications for the scenario (App choosing component) Applications configuration-SW;
 a processor adapted to:
  (i) activate said software stored in said data storage; and
  ii) receive said environmental data using scenario-based algorithms and to output sound data; and
 a portable communication device associated with the sight-disabled user, said device adapted to receive said sound data from said processor, associated with said environmental data, and wherein said scenario identification component is configured to provide said user with specific Apps from an App choosing component, in accordance with said scenario in which said user is currently found, and based on said user's identity and further wherein said device is adapted to convert the sound data into brain-interpretable sound for the sight-disabled user to provide him/her with a real-time understanding of said environment.

2. The system according to claim 1, wherein said portable communication device outputs scenario-based stereophonic sounds to represent distance and direction from objects in a vicinity of said user, thereby enabling the user to navigate his environment.

3. The system according to claim 2, wherein said stereophonic sounds processed using said scenario-based algorithms provide said user with information relating to said distance and direction from the object, based on a delay of sound between a right ear and a left ear of said user.

4. The system according to claim 2, wherein said device is configured to adjust the volume of said stereophonic sounds, responsive to said distance.

5. A system according to claim 1, further comprising an algorithm or component for context scenario identification, and an algorithm or component for scenario decision making, based on the identity of the user, wherein said components/algorithms update each other, to output an optimized selection of Apps or only one App for said user, based on criteria reflecting the identity of said user and said scenario.

6. A method for processing scenario-based information concerning an environment of a sight-disabled user, the method comprising:
 gathering information and environmental data from sensors on a user device, said data associated with objects in a vicinity of the user;
 activating a scenario identification component and an App choosing component;
 providing the user with specific Apps from said App choosing component based on said user's identity and responsive to said scenario, in which said user is currently found;
 processing said information using scenario-based algorithms and data to output associated sound data; and
 converting said sound data associated with said environmental data into scenario-based brain-interpretable sound for the sight-disabled user to provide him/her with a real-time understanding of said environment.

7. The method according to claim 6, wherein said processing using scenario-based algorithms and said converting step outputs stereophonic sounds to represent distance and direction from objects in a vicinity of said user, thereby enabling the user to navigate his/her environment.

8. The method according to claim 7, wherein said stereophonic sounds provide said user with scenario-based information relating to said distance and direction from at least one of the objects, based on a delay of sound between a right ear and a left ear of said user.

9. The method according to claim 8, wherein said device is configured to adjust the volume of said scenario-based stereophonic sounds, responsive to said distance.

10. The method of claim 9, wherein said scenario-based stereophonic sounds provide said direction to the at least one object based on said delay of sound between the right ear and the left ear of said user and an indication of said distance by a periodicity of periodic sounds, wherein closer objects are represented by shorter period of the periodic sounds.

11. The method of claim 10, wherein said scenario-based stereophonic sounds provide the direction to the at least one object, based on the delay of sound between the right ear and the left ear and the distance by the frequency of sounds, wherein closer objects are represented by higher frequency sounds.

12. The method of claim 6, wherein said scenario-based algorithms further outputting voice-read texts, by implementing an optical character recognition (OCR) algorithm.

13. The method of claim 12, wherein said OCR information is from a camera on a personal device of the user and wherein said camera is used for said OCR and further for playback texts in the vicinity of said user.

14. The method of claim 13, wherein said scenario-based algorithms combine voice identification of objects by using an artificial intelligence (A.I.) algorithm disposed on the personal device.

15. The method of claim 14, wherein said information from the camera is used to identify objects by the A.I and playback the names of the objects that are in said vicinity.

16. The method of claim 15, wherein said A.I algorithm comprises a face recognition algorithm, adapted to work on images captured by said camera.

17. The method of claim 6, wherein said information from different directions or purposes is processed using said scenario-based algorithms and is outputted by different voices and tunes so that the user is able to identify and distinguish between information from different directions and/or sources.

18. The method of claim 17, wherein said scenario-based algorithms that process the sensors data are orientation dependent.

19. The method of claim 8, wherein said gathering step comprises at least one of: gathering data from different coverage areas; employing scanning sensors which scan in mechanical or digital ways; and using sensors which scope wide angles and gather the data, which is split to be processed part by part.

20. The method of claim 6, wherein said information from each sensor is processed differently, based on the scenario and the sensor direction or placement.

21. The method of claim 20, using echo and noise cancelation so that the scenario-based algorithms remove sounds that are identified as noises and the user get the surround sound information clearly.

22. The method according to claim 6, comprising implementing at least two software parts, executable by at least one hardware processor to perform the method;
 a first software part comprising software to select scenario identification, wherein the scenarios is depicted by any method selected from:
 intervention or commands from the user;
 policy derived selection; and
 Context derived by AI decision based on the data that are collected from sensors; and
 a second software part configured to implement algorithms or apps that make an implementation of the scenario-based program.

23. A method according to claim 6, further comprising activating:
 a) an algorithm or component for context scenario identification; and
 b) an algorithm or component for scenario decision making, based on the identity of the user, wherein said components/algorithms update each other, to output an optimized selection of Apps or only one App for said user, based on criteria reflecting the identity of said user and said scenario.

* * * * *